US007267940B2

(12) United States Patent
Chen et al.

(10) Patent No.: US 7,267,940 B2
(45) Date of Patent: Sep. 11, 2007

(54) HSV-2 TYPE-SPECIFIC IMMUNOASSAYS USING GLYCOPROTEIN G2 PEPTIDES

(75) Inventors: Peilin Chen, Cupertino, CA (US); Peter Su, Mercer Island, WA (US); Hao Yu, Pacheco, CA (US); Lawrence J. Blecka, Walnut Creek, CA (US); Patrick F. Coleman, Edmonds, WA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 323 days.

(21) Appl. No.: 10/382,085

(22) Filed: Mar. 4, 2003

(65) Prior Publication Data

US 2004/0175753 A1    Sep. 9, 2004

(51) Int. Cl.
*A61K 39/245* (2006.01)
*C07K 14/035* (2006.01)
*G01N 33/543* (2006.01)
*G01N 33/546* (2006.01)
*G01N 33/53* (2006.01)
*C12Q 1/70* (2006.01)

(52) U.S. Cl. .......................... 435/5; 530/324; 435/7.1; 436/518; 436/533

(58) Field of Classification Search ................ 530/324; 436/518, 533; 435/5, 7.1; 930/224
See application file for complete search history.

(56) References Cited

U.S. PATENT DOCUMENTS

| 4,745,182 | A |   | 5/1988  | Cohen et al.          |
|-----------|---|---|---------|-----------------------|
| 4,764,459 | A |   | 8/1988  | Hampar et al.         |
| 5,229,490 | A | * | 7/1993  | Tam ............... 530/324 |
| 5,260,189 | A | * | 11/1993 | Formoso et al. ........ 435/5 |
| 5,554,728 | A | * | 9/1996  | Basava et al. ......... 530/327 |
| 5,919,616 | A |   | 7/1999  | Aurelian et al.       |
| 5,965,357 | A |   | 10/1999 | Marsden               |
| 6,773,812 | B2| * | 8/2004  | Chandler et al. ....... 428/403 |
| 6,821,519 | B2| * | 11/2004 | Day et al. ............ 424/231.1 |

FOREIGN PATENT DOCUMENTS

WO    WO98/03543    *    1/1998

OTHER PUBLICATIONS

Publication Site for Issued and Published Sequences (PSIPS) View Sequence for U.S. Appl. No. 6,821,519, SEQ ID No. 253, downloaded from http://seqdata.uspto.gov, on Apr. 12, 2006.*
NCBI, protein sequence information for bovine serum albumin, Accession No. CAA76847, downloaded from www.ncbi.nlm.nih.gov, on Apr. 13, 2006.*
Pierce Chemical Company, Instructions for Imject Carrier Proteins BSA, KLH and OVA, Sep. 1998, downloaded from http://www.piercenet.com.*

Lee et al., "Detection of Herpes Simplex Virus Type 2-Specific Antibody with Glycoprotein G", *Journal of Clinical Microbiology* 22:4: 641-644 (1985).
Eis-Hubinger et al., "Evaluation of Three Glycoprotein G2-Based Enzyme Immunoassays for Detection of Antibodies to Herpes Simplex Virus Type 2 in Human Sera", *Journal of Clinical Microbiology* 37:5: 1242-1246 (1999).
Ashley et al., "Genital Herpes: Review of the Epidemic and Potential Use of Type-Specific Serology", *Clinical Microbiology Reviews* 12:1: 1-8 (1999).
Groen et al., "Comparison of Two Enzyme-Linked Immunosorbent Assays and One Rapid Immunoblot Assay for Detection of Herpes Simplex Virus Type 2-Specific Antibodies in Serum", *Journal of Clinical Microbiology* 36:3: 845-847 (1998).
Ashley et al., "Premarket Evaluation of a Commercial Glycoprotein G-Based Enzyme Immunoassay for Herpes Simplex Virus Type-Specific Antibodies", *Journal of Clinical Microbiology* 36:1: 294-295 (1998).
Ackermann et al., "Mapping of Linear Antigenic Determinants on Glycoprotein C of Herpes Simplex Virus Type 1 and Immunoglobulin G Antibodies", *Journal of Medical Virology* 55: 281-287 (1998).
Levi et al., "Peptide Sequences of Glycoprotein G-2 Discriminate between Herpes Simplex Virus Type 2 (HSV-2) and HSV-1 Antibodies", *Clinical and Diagnostic Laboratory Immunology* 3:3: 265-269 (1996).
Liljeqvist et al., "Localization of type-specific epitopes of herpes simplex virus type 2 glycoprotein G recognized by human and mouse antibodies", *Journal of General Virology* 79: 1215-1224 (1998).
Grabowska et al., "Identification of type-specific domains within glycoprotein G of herpes simplex virus type 2 (HSV-2) recognized by the majority of patients infected with HSV-2, but not by those infected with HSV-1", *Journal of General Virology* 80: 1789-1798 (1999).
Marsden et al., "Identification of an Immunodominant Sequential Epitope in Glycoprotein G of Herpes Simples Virus Type 2 That is Useful for Serotype-Specific Diagnosis", *Journal of Medical Virology* 56: 79-84 (1998).
Hashido et al, "Detection of Herpes Simplex Virus Type-Specific Antibodies by an Enzyme-Linked Immunosorbent Assay Based on Glycoprotein G", *Journal of Medical Virology* 53: 319-323 (1997).
Brugha et al., "Genital Herpes Infection: A Review," *International Journal of Epidemiology* vol. 26, No. 4, 698-709 (1997).

* cited by examiner

*Primary Examiner*—Long V. Le
*Assistant Examiner*—Christine Foster
(74) *Attorney, Agent, or Firm*—Townsend and Townsend and Crew LLP

(57) ABSTRACT

The present invention relates to peptides that are derived from HSV-2 glycoprotein G2 and represent HSV-2 type-specific epitopes. The present invention also provides for compositions comprising these peptides for type-specific serological diagnosis of HSV-2 infection. Methods of using these peptides for type-specific detection of HSV-2 antibodies and differentiation of HSV-2 viral infection from HSV-1 and other herpes family viral infections are further provided.

60 Claims, 6 Drawing Sheets

Fig. 1 SEQ ID NO:1

$_1$PGSPAPPPPEHRGGPEEFEGAGDGEPPEDDDSATGL$_{36}$

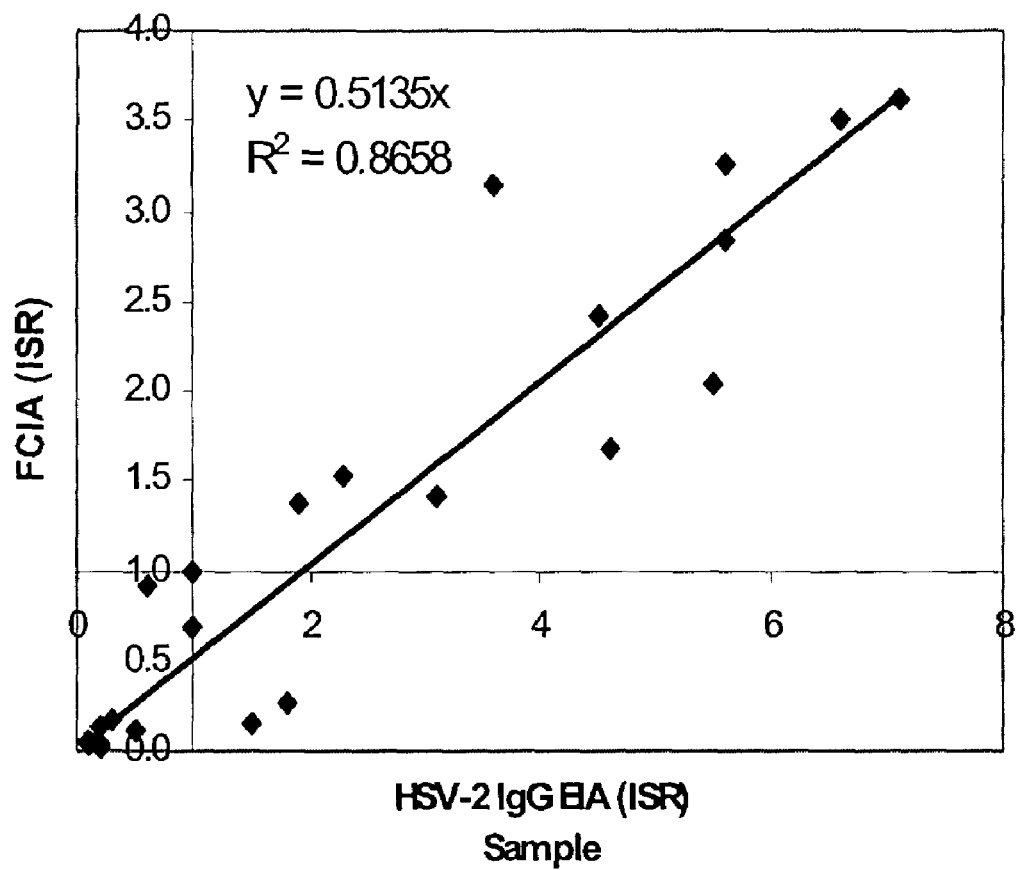

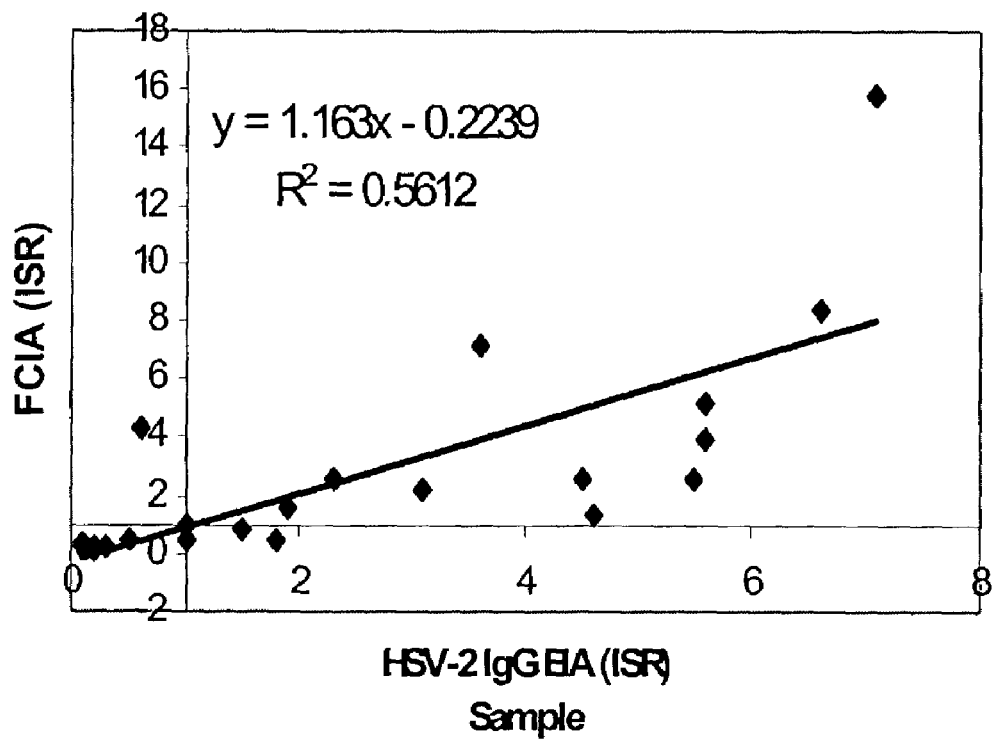

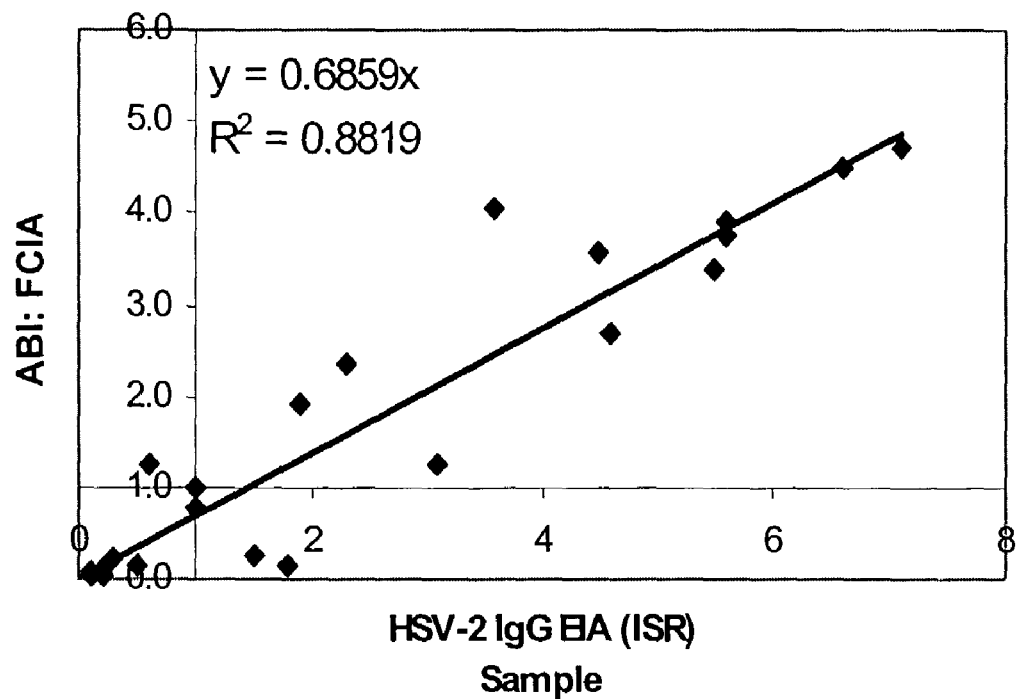

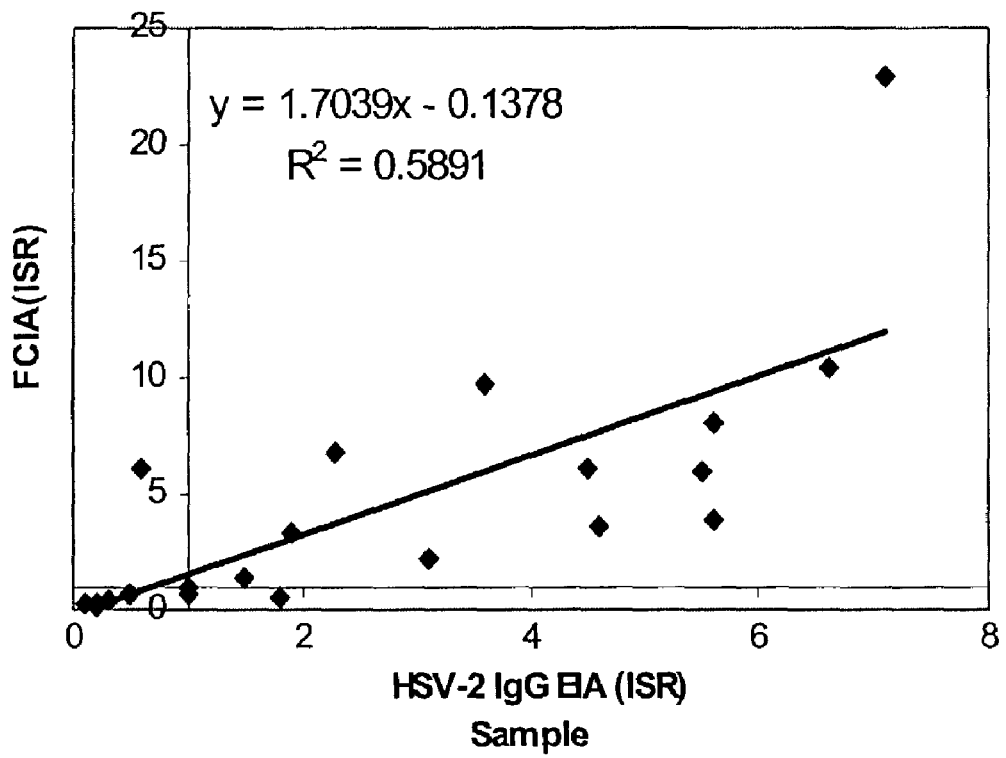

SCHEME 1

HSV-2 TYPE-SPECIFIC IMMUNOASSAYS USING GLYCOPROTEIN G2 PEPTIDES

BACKGROUND OF THE INVENTION

Genital herpes, caused by infection with herpes simplex virus type 2 (HSV-2), is the most common sexually transmitted disease in humans. The current prevalence of HSV-2 infections is greater than 20% among adults in the United States (Ashley and Wald, *Clin. Microbiol. Rev.* 12:1-8, 1999). This disease is a major concern in public health due to its morbidity, frequency of recurrence, and life-threatening severity in the case of newborns infected with the virus following intrapartum transmission.

The serological diagnosis for HSV-2 infection has been hampered, however, by the fact that there exists extensive cross-reactivity of HSV-2 antibodies to herpes simplex virus type 1 (HSV-1). The two subtypes of HSV have important differences in epidemiology and natural history: HSV-1 usually causes orolabial disease, whereas HSV-2 almost always leads to genital disease. For a general review of HSV epidemiology and diagnosis, see Brugha et al., *Int. J. Epidemiol.* 26:698-709, 1997; Ashley and Wald, supra.

Various approaches have been developed in an effort to identify HSV-2 specific antibodies. The most reliable method for a type-specific detection of HSV-2 antibodies to date is an immunoblot assay, preferably a Western blot assay. The significant drawback of this method is that the procedure is labor-intensive and requires the investigator to have a certain level of skill in order to achieve unequivocal results. In the last decade or so, several HSV glycoproteins have been identified as the viral proteins that contain type-specific epitopes. Immunoassays have been developed based on these glycoproteins for type-specific determination of HSV-2 infection. See, e.g., Lee et al., *J. Clin. Microbiol.* 22:641-644 (1985); Eis-Hubinger et al., *J. Clin. Microbiol.* 37:1242-1246 (1999); Groen et al., *J. Clin. Microbiol.* 36:845-847 (1998); Ashley et al., *J. Clin. Microbiol.* 36:294-295 (1998); Hashido et al., *J. Med. Virol.* 53:319-323 (1997); and U.S. Pat. No. 4,764,459.

As these methods show a varying degree of sensitivity and specificity, there is one common problem associated with these glycoprotein-based immunoassays for HSV-2 antibody type-specific detection. The full length glycoproteins are obtained through isolation of either naturally-occurring viral proteins or recombinantly expressed proteins. These procedures can be costly and susceptible to impurities and thus cross-reactivity.

Studies have indicated that peptides corresponding to partial sequences of certain viral proteins of HSV-2 may be useful in HSV-2 type-specific detection, as these peptides may represent some HSV-2 type-specific epitopes. See, e.g., Levi et al., *Clin. Diagn. Lab. Immunol.* 3:265-269 (1996); Ackermnann et al., *J. Med. Virol.* 55:281-287 (1998); Marsden et al., *J. Med. Virol.* 56:79-84 (1998); Lijeqvist et al., *J Gen. Virol* 79:1215-1224 (1998); Grabowska et al., *J. Gen. Virol.* 80:1789-1798 (1999); U.S. Patent Nos. 5,919,616 and 5,965,357. The present invention provides novel peptide sequences of HSV-2 glycoprotein G2 that can be used in HSV-2 type-specific diagnosis.

All items of published literature and patents cited in the specification are hereby incorporated herein by reference.

BRIEF SUMMARY OF THE INVENTION

In one aspect, the present invention relates to a composition containing a peptide that binds specifically to HSV-2 antibodies and reacts minimally to HSV-1 specific antibodies or antibodies to any other herpes family viruses. This peptide consists of 24 to 36 contiguous amino acids of SEQ ID NO:1. In one preferred embodiment, the peptide has a sequence consisting of amino acids 5 to 32 of SEQ ID NO:1. In a more preferred embodiment, the peptide has a sequence consisting of amino acids 9 to 32 of SEQ ID NO:1. In a most preferred embodiment, the peptide has an amino acid sequence of SEQ ID NO:1.

In some embodiments, the peptide is dimerized. Such dimerization may be achieved via a disulfide bond. In other embodiments, the peptide is linked to a carrier. Examples of suitable carriers are carboxylated microspheres, preferably carboxylated latex or magnetic microspheres.

In some embodiments, the peptide is linked to a carrier via a linker at the N-terminus or the C-terminus of the peptide, whereas in other embodiments the peptide is linked to a carrier via a linker at an internal amino acid residue of the peptide. In some cases, the linker is or includes a heterologous peptide. In others, the linker is or includes a heterologous protein. In still other cases, both a heterologous protein and a heterologous peptide are used. In some other embodiments, the entire linker is a heterologous peptide. In one preferred embodiment, the heterologous protein is bovine serum albumin (BSA), whereas in another preferred embodiment, the heterologous protein is Keyhole Limpet Hemocyanin (KLH). In some embodiments, the heterologous peptide includes one cysteine residue, one lysine residue, and at least two glycine residues. In some other embodiments, the linker includes a branched amino acid polymer, whose structure is preferably that. shown below:

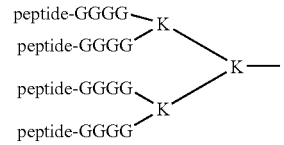

In one preferred embodiment, the peptide has an amino acid sequence of SEQ ID NO:1, the carrier is a carboxylated magnetic microsphere, the linker includes 4-(maleimidomethyl)-1-cyclohexanecarboxylic acid (SMCC) and a heterologous peptide with an amino acid sequence of GGCK (SEQ ID NO:2), and the heterologous peptide is attached to the peptide at the C-terminus of the peptide. In other preferred embodiments, the linker further includes the heterologous protein BSA directly attached to the carrier, and SMCC is attached to BSA and, via the heterologous peptide, to the peptide.

In another preferred embodiment, the peptide has an amino acid sequence consisting of amino acids 5 to 32 of SEQ ID NO:1, the carrier is a carboxylated magnetic microsphere, the linker includes SMCC and a heterologous peptide with an amino acid sequence of GGGGCK (SEQ ID NO:3), and the heterologous peptide is attached to the peptide at the C-terminus of the peptide. In other preferred embodiments, the linker further includes the heterologous protein BSA directly attached to the carrier, and SMCC is attached to BSA and, via the heterologous peptide, to the peptide.

In yet another preferred embodiment, the peptide has an amino acid sequence consisting of amino acids 9 to 32 of SEQ ID NO:1, the carrier is a carboxylated magnetic microsphere, the linker includes SMCC and a heterologous peptide with an amino acid sequence of GGGGCK (SEQ ID NO:3), and the heterologous peptide is attached to the peptide at the C-terminus of the peptide. In other preferred embodiments, the linker further includes the heterologous protein BSA directly attached to the carrier, and SMCC is attached to BSA and, via the heterologous peptide, to the peptide.

In still another preferred embodiment, the peptide has an amino acid sequence consisting of amino acids 9 to 32 of SEQ ID NO:1, the carrier is a carboxylated magnetic microsphere, the linker includes SMCC and a heterologous peptide with an amino acid sequence of KCGGGG (SEQ ID NO:4), and the heterologous peptide is attached to the peptide at the N-terminus of the peptide. In other preferred embodiments, the linker further includes the heterologous protein BSA directly attached to the carrier, and SMCC is attached to BSA and, via the heterologous peptide, to the peptide.

In one further preferred embodiment, the peptide has an amino acid sequence consisting of amino acids 9 to 32 of SEQ ID NO:1, the carrier is a carboxylated microsphere, and the linker includes a branched amino acid polymer that has the following structure and further includes a short peptide of CK, which via the C residue is directly attached to the last K residue of the structure:

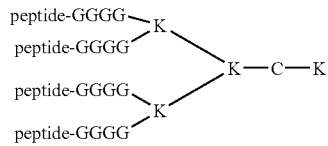

In a second aspect, the present invention relates to a method for type-specific diagnosis of HSV-2 infection. The method for specific detection of HSV-2 antibodies in a biological sample includes two steps. The first step is contacting the biological sample with a composition that includes a peptide consisting of 24 to 36 contiguous amino acids of SEQ ID NO:1, linked to a carrier. The second step is detecting whether antigen-antibody binding has occurred between the peptide and an antibody component of the biological sample. In this step, the detection of antigen-antibody binding indicates the presence of HSV-2 antibodies in the biological sample. In some preferred embodiments, the second step is performed by flow cytometry. It is also preferred that the biological sample be whole blood, serum, plasma, cerebrospinal fluid, tissue from a swab device, or vesicle fluid.

In one preferred embodiment, the peptide has a sequence consisting of amino acids 5 to 32 of SEQ ID NO:1. In a more preferred embodiment, the peptide has a sequence consisting of amino acids 9 to 32 of SEQ ID NO:1. In a most preferred embodiment, the peptide has an amino acid sequence of SEQ ID NO:1.

In some embodiments, the peptide is dimerized. Such dimerization may be achieved via a disulfide bond. In some other embodiments, the peptide is linked to a carboxylated microsphere, preferably a carboxylated latex or magnetic microsphere.

In some embodiments, the peptide is linked to the carrier via a linker at the N-terminus or the C-terminus of the peptide, whereas in other embodiments the peptide is linked to a carrier via a linker at an internal amino acid residue of the peptide. In some embodiments, the linker includes a heterologous peptide. In some other embodiments, the linker includes a heterologous protein. In some other embodiments, the linker includes a heterologous protein in addition to a heterologous peptide. In some other embodiments, the linker is a heterologous peptide. In one preferred embodiment, the heterologous protein is BSA, whereas in another preferred embodiment, the heterologous protein is KLH. In some embodiments, the heterologous peptide includes one cysteine residue, one lysine residue, and at least two glycine residues. In some other embodiments, the linker includes a branched amino acid polymer, whose structure is preferably that shown below:

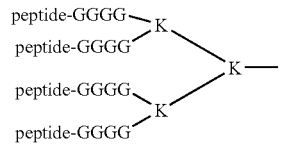

In one preferred embodiment, the peptide has an amino acid sequence of SEQ ID NO:1, the carrier is a carboxylated magnetic microsphere, the linker includes SMCC and a heterologous peptide with an amino acid sequence of GGCK (SEQ ID NO:2), the heterologous peptide is attached to the peptide at the C-terminus of the peptide, and the detection of antigen-antibody binding is achieved by flow cytometry. In other preferred embodiments, the linker further includes the heterologous protein BSA directly attached to the carrier, and SMCC is attached to BSA and, via the heterologous peptide, to the peptide.

In another preferred embodiment, the peptide has an amino acid sequence consisting of amino acids 5 to 32 of SEQ ID NO:1, the carrier is a carboxylated magnetic microsphere, the linker includes SMCC and a heterologous peptide with an amino acid sequence of GGGGCK (SEQ ID NO:3), the heterologous peptide is attached to the peptide at the C-terminus of the peptide, and the detection of antigen-antibody binding is achieved by flow cytometry. In other preferred embodiments, the linker further includes the heterologous protein BSA directly attached to the carrier, and SMCC is attached to BSA and, via the heterologous peptide, to the peptide.

In yet another preferred embodiment, the peptide has an amino acid sequence consisting of amino acids 9 to 32 of SEQ ID NO:1, the carrier is a carboxylated magnetic microsphere, the linker includes SMCC and a heterologous peptide with an amino acid sequence of GGGGCK (SEQ ID NO:3), the heterologous peptide is attached to the peptide at the C-terminus of the peptide, and the detection of antigen-antibody binding is achieved by flow cytometry. In other preferred embodiments, the linker further includes the heterologous protein BSA directly attached to the carrier, and SMCC is attached to BSA and, via the heterologous peptide, to the peptide.

In still another preferred embodiment, the peptide has an amino acid sequence consisting of amino acids 9 to 32 of SEQ ID NO:1, the carrier is a carboxylated magnetic microsphere, the linker includes SMCC and a heterologous peptide with an amino acid sequence of KCGGGG (SEQ ID NO:4), and the heterologous peptide is attached to the peptide at the N-terminus of the peptide. In other preferred embodiments, the linker further includes the heterologous protein BSA directly attached to the carrier, and SMCC is attached to BSA and, via the heterologous peptide, to the peptide.

In one further preferred embodiment, the peptide has an amino acid sequence consisting of amino acids 9 to 32 of SEQ ID NO:1, the carrier is a carboxylated microsphere, and the linker includes a branched amino acid polymer that has the following structure and further includes a short peptide of CK, which via the C residue is directly attached to the last K residue of the structure:

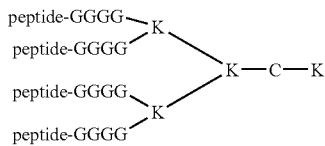

BRIEF DESCRIPTION OF THE DRAWINGS

FIG. 1 shows SEQ ID NO:1, $_1$PGSPAPPPPEHRGG-PEEFEGAGDGEPPEDDDSATGL$_{36}$

FIG. 2 shows the correlation between HSV-2 specific antibody detection using a commercial HSV-2 type-specific enzyme-linked immunoassay and using the method of the present invention where peptide 1-SMCC-BSA conjugate, (PGSPAPPPPEHRGGPEEFE-GAGDGEPPEDDDSATGLGGCK)-SMCC-BSA (SEQ ID NO:5), is used as an HSV-2 specific antigen.

FIG. 3 shows the correlation between HSV-2 specific antibody detection using a commercial HSV-2 type-specific enzyme-linked immunoassay and using the method of the present invention where peptide 2-SMCC-BSA conjugate, (APPPPEHRGGPEEFEGAGDGEPPEDDDSGGGCK)-SMCC-BSA, (SEQ ID NO:6), is used as an HSV-2 specific antigen.

FIG. 4 shows the correlation between HSV-2 specific antibody detection using a commercial HSV-2 type-specific enzyme-linked immunoassay and using the method of the present invention where BSA-SMCC-peptide 5 conjugate, BSA-SMCC-(KCGGGGPEHRGGPEEFEGAGDGEPPED-DDS) (SEQ ID NO:7), is used as an HSV-2 specific antigen.

FIG. 5 shows the correlation between HSV-2 specific antibody detection using a commercial HSV-2 type-specific enzyme-linked immunoassay and using the method of the present invention where peptide 5, KCGGGGPEHRGG-PEEFEGAGDGEPPEDDDS (SEQ ID NO:8), is used as an HSV-2 specific antigen.

DETAILED DESCRIPTION OF THE INVENTION

I. Introduction

Figure 6:
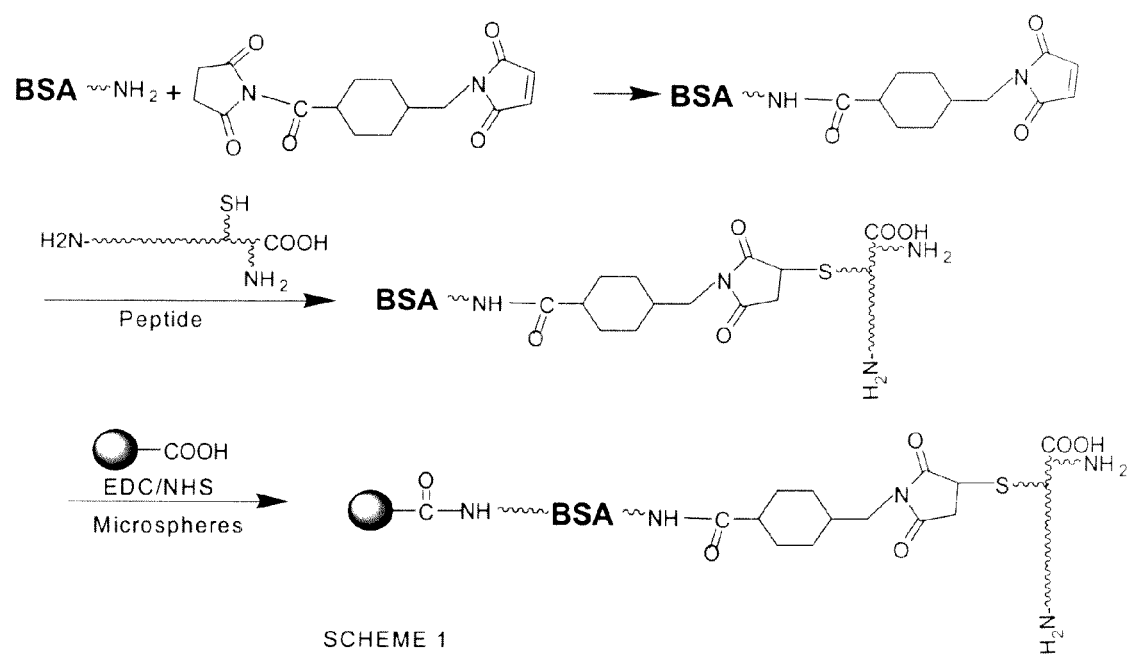
FIG. 6 shows an illustrative process of conjugating an HSV-2 peptide via a heterologous peptide already attached at its C-terminus to SMCC, which is in turn attached to a microsphere via BSA.

The present invention relates to peptides that consist of partial sequences of HSV-2 glycoprotein G2 and represent HSV-2 type-specific epitopes. Experiments have shown that HSV-2 peptides consisting of 24 to 36 contiguous amino acids of SEQ ID NO:1 bind HSV-2 antibodies with high specificity and sensitivity, while their cross-reactivity to HSV-1 antibodies is minimal. Thus these peptides are useful for type-specific serological diagnosis of HSV-2 infection, particularly for differentiation of HSV-2 infection from HSV-1 infection.

Compositions comprising peptides of the present invention are also provided for type-specific serological diagnosis of HSV-2 infection. In preferred embodiments, the peptides of the present invention are linked to a carrier, such as a carboxylated latex or magnetic microsphere, via a linker that includes a heterologous peptide and/or protein, such as bovine serum albumin (BSA) and Keyhole Limpet Hemocyanin (KLH). Other linkers, such as branched amino acid polymers, straight or branched-chain carbon linkers, heterocyclic carbon linkers (e.g., SMCC), or polyether linkers, may also be used in practicing the present invention. An HSV-2 peptide of this invention may be conjugated to a carrier at the N-or C-terminus of the peptide, or via an internal amino acid residue.

Furthermore, methods for using these peptides for type-specific detection of HSV-2 antibodies are provided. In preferred embodiments, the detection of HSV-2 specific antibodies is performed by flow cytometry.

II. Definitions

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The term "amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. An HSV-2 peptide as used in the present application refers to a peptide that has a sequence corresponding to a segment of the HSV-2 glycoprotein G2.

A "carrier" as used herein refers to an inert solid support of natural material, such as glass and collagen, or synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. Frequently, some functional groups, e.g., carboxylic acid (—COOH), free amine (—NH2), and sulfhydryl (—SH) groups, naturally present on the surface of a carrier can be used for peptide linkage. In case no such functional group is naturally available, a desired functional group, such as a carboxylic acid group, or a moiety known to be a partner of a binding interaction (such as avidin that is capable of binding biotin) may be attached to such solid support. A preferred carrier of the present invention is a carboxylated latex or magnetic microsphere.

A "linker" as used herein refers to any means of connecting a peptide of the present invention to a carrier. The linkage may be located at either the N-terminus or the C-terminus of the peptide. In some embodiments, the linkage can be effectuated through a side group of an internal amino acid residue of the peptide, such as a second carboxyl group of an aspartate residue that is not located at the N-or C-terminus of the peptide. A linker may comprise a peptide (e.g., the short amino acid sequence of GGGGCK (SEQ ID NO:3) or GGCK (SEQ ID NO:2)) or a protein (e.g., BSA or KLH) that is heterologous to the peptide of the present invention. In addition to a heterologous peptide, a linker may further comprise a heterologous protein, such as BSA or KLH. Non-polypeptide linkers, such as straight or branched-chain carbon linkers, heterocyclic carbon linkers, or polyether linkers, may also be suitable for the purpose of connecting a peptide of the invention to a carrier, or as a part of a multiple-component linker. One preferred non-polypeptide linker is SMCC. Moreover, a linker may comprise a branched amino acid polymer that is capable of attaching more than one peptide of the invention to a carrier. Both heterobifunctional and monobifunctional linkers are suitable in the practice of the present invention. A linker may also comprise a covalent bond, such as a peptide bond or a disulfide bond, or a noncovalent bond, such as an ionic or hydrophobic bond, in the case where a peptide of the present invention is attached directly to a carrier. An example of a non-covalent bond is the interaction between antigen-antibody or biotin-avidin.

The term "heterologous" when used in the context of describing a peptide or a protein as a linker or a component of a linker indicates that the linker peptide or linker protein and the peptide of the invention, which is connected to the carrier via the linker, are not found in the same relationship with one another in nature. In other words, the linker peptide and/or linker protein and the peptide of the invention, as they are conjugated in any particular embodiment of the present invention, do not produce an amino acid sequence that is found in nature. As an example, the peptides of the present invention are derived from HSV-2 glycoprotein G2, a heterologous peptide or protein is therefore not derived from any sequence of HSV-2 glycoprotein G2 that is contiguous to the sequence from which the peptides of the present invention are derived.

"Specific detection" as used herein refers to the fact that detection of any antibody bound to the peptides of the present invention is determinative of the presence of HSV-2 antibody, often in a heterogeneous population of other antibodies and proteins. In particular, the presence of HSV-1 antibodies will not result in a detectable amount of antibody bound to the peptides. Hence, the term "specific detection" particularly encompasses the use of HSV-2 peptides of the present invention to differentiate HSV-2 infection from HSV-1 infection. Under designated immunoassay conditions, a detectable signal is designated as one that is at least twice the background signal. Thus, specific antibody-peptide binding should yield a signal at least two times, preferably more than 10 times, and more preferably more than 100 times the background.

The term "dimerized" or "dimer" when used to describe a peptide of the present invention refers to the complex formed by two molecules comprising the same peptide via a covalent bond, such as a disulfide bond, or a noncovalent bond, such as via the binding interaction between a known tag and tag-binder pair (e.g., biotin and avidin). The covalent bond or noncovalent bond typically occurs between the linker portions of the two peptide-containing molecules.

The term "an internal amino acid residue" as used herein refers to any amino acid residue that is not the first residue from either the N-terminus or the C-terminus of an HSV-2 peptide of the present invention.

The term "biological sample" refers to sections of tissues such as biopsy and autopsy samples, and frozen sections taken for histological purposes. Such samples may include whole blood, serum, plasma, cerebrospinal fluid, sputum, tissue, cultured cells, e.g., primary cultures, explants, transformed cells, stool, urine, vesicle fluid, mucus, and other bodily secretion, or tissue that could be sampled with a swab device. A biological sample is typically obtained from a human who may have been infected with HSV-2.

The term "antibody" denotes a protein of the immunoglobulin family or a polypeptide including fragments of an immunoglobulin that is capable of noncovalently, reversibly, and in a specific manner binding a corresponding antigen. An illustrative antibody structural unit includes a tetramer. Each tetramer is composed of two identical pairs of polypeptide chains, each pair having one "light" (about 25 kD) and one "heavy" chain (about 50-70 kD), connected through one or more disulfide bonds. The recognized immunoglobulin genes include the $\kappa$, $\lambda$, $\alpha$, $\delta$, $\gamma$, $\epsilon$, and $\mu$ constant region genes, as well as the myriad immunoglobulin variable region genes. Light chains are classified as either $\kappa$ or $\lambda$ Heavy chains are classified as $\gamma$, $\mu$, $\alpha$, $\delta$, or $\epsilon$ which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively.

The term "complementarity-determining domains" or "CDRs" refers to the hypervariable regions of $V_l$ and $V_H$. The CDR is the target protein-binding site of the antibody chain that harbors specificity for that target protein. There are three CDRs (CDR1-3numbered sequentially from the N-terminus) in each human $V_L$ or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, *Immunology,* 4th ed., Chapter 4, W.H. Freeman & Co., New York, 2000).

The positions of the CDRs and framework regions are determined using various well known definitions in the art, e.g., Kabat, Chothia, International ImMunoGeneTics database (IMGT), and AbM (see, e.g., Johnson et al., *Nucleic Acids Res.,* 29:205-206 (2001); Chothia and Lesk, *J. Mol. Biol.,* 196:901-917 (1987); Chothia et al., *Nature,* 342:877-883 (1989); Chothia et al., *J. Mol. Biol.,* 227:799-817 (1992); Al-Lazikani et al., *J. Mol.Biol.,* 273:927-748 (1997)). Definitions of antigen combining sites are also described in the following: Ruiz et al., *Nucleic Acids Res.,* 28:219-221 (2000); and Lefranc, M. P., *Nucleic Acids Res.,* 29:207-209 (2001); MacCallum et al., *J. Mol. Biol.,* 262:732-745 (1996); and Martin et al, *Proc. Natl. Acad. Sci. USA,* 86:9268-9272 (1989); Martin et al., *Methods Enzymol.,* 203:121-153 (1991); and Rees et al., In Sternberg M. J. E. (ed.), *Protein Structure Prediction*, Oxford University Press, Oxford, 141-172 (1996).

The terms "antibody light chain" and "antibody heavy chain" denote the $V_L$ or $V_H$, respectively. The $V_L$ is encoded by the gene segments V (variable) and J (junctional), and the $V_H$ is encoded by V, D (diversity), and J. Each of $V_L$ or $V_H$ includes the CDRs as well as the framework regions.

Antibodies exist as intact immunoglobulins or as a number of well-characterized fragments produced by digestion with various peptidases. Thus, for example, pepsin digests an antibody below the disulfide linkages in the hinge region to produce $F_{(ab)}'_2$, a dimer of $F_{ab}'$ which itself is a light chain joined to $V_H$-$C_H$1 by a disulfide bond. The $F_{(ab)}'_2$ may be reduced under mild conditions to break the disulfide linkage in the hinge region, thereby converting the $F_{(ab)}'_2$ dimer into an $F_{ab}'$ monomer. The $F_{ab}'$ monomer is essentially $F_{ab}$ with part of the hinge region (Paul, *Fundamental Immunology* 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain $F_v$) or those identified using phage display libraries (see, e.g., McCafferty et al., *Nature,* 348:552-554 (1990))

For preparation of monoclonal or polyclonal antibodies, any technique known in the art can be used (see, e.g., Kohler & Milstein, *Nature,* 256:495-497 (1975); Kozbor et al., *Immunology Today,* 4:72 (1983); Cole et al., *Monoclonal Antibodies and Cancer Therapy*, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies, and heteromeric $F_{ab}$ fragments, or scFv fragments that specifically bind to selected antigens (see, e.g., McCafferty et al., supra; Marks et al., *Biotechnology,* 10:779-783, (1992)).

An "HSV-2 antibody" as used in this application refers to an antibody that is specifically reactive to HSV-2 antigens but not to antigens of any other source, particularly HSV-1.

III. Synthesis of Peptides

A. Synthesis of Peptides by Chemical Methods

The peptides of the present invention may be synthesized chemically using conventional peptide synthesis or other protocols well known in the art.

Peptides may be synthesized by solid-phase peptide synthesis methods using procedures similar to those described by Merrifield et al., *J. Am. Chem. Soc.,* 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach,* IRL Press (1989), and Bodanszky, *Peptide Chemistry, A Practical Textbook,* 2nd Ed., Springer-Verlag (1993)).

B. Producing Peptides by Recombinant Methods

As one skilled in the art will know, the peptides of the present invention can also be generated by recombinant means. Although it is often preferred to have the peptides synthesized chemically, according to the methods described above, there may be some advantages to obtain the peptides recombinantly in certain cases. For example, when an HSV-2 peptide of the present invention is to be conjugated with a heterologous peptide and/or a heterologous protein, the nucleic acid sequence encoding the HSV-2 peptide can be introduced into a suitable expression vector, and subsequently fused in-frame with the coding sequence(s) of the heterologous peptide and/or protein, so that upon transfection or transformation of an appropriate host cell line, the fusion polypeptide of the HSV-2 peptide and the heterologous peptide/protein can be produced and purified. A large variety of expression vectors and host cells well known to those skilled in the art can be used for this purpose.

C. Purification of Peptides

Purification of synthetic peptides is accomplished using various methods of chromatography, such as reverse phase HPLC, gel permeation, ion exchange, size exclusion, affinity, partition, or countercurrent distribution. The choices of appropriate matrices and buffers are well known in the art.

Purification of recombinantly produced peptides to substantial purity can be accomplished using standard techniques including selective precipitation with such substances as ammonium sulfate, column chromatography, immunopurification methods and others. See, e.g., Scopes, *Protein Purification: Principles and Practice* (1982); U.S. Pat. No. 4,673,641; Ausubel et al., *Current Protocols in Molecular Biology* (1994); and Sambrook and Russell, *Molecular Cloning: A Laboratory Manual* 3d Ed. (2001). In particular, when a recombinant polypeptide comprises an HSV-2 peptide fused to a heterologous protein with known molecular adhesion properties, it can be purified with relative ease and to a relatively high purity by passing through a column to which a proper binding partner is immobilized.

D. Confirmation of Peptide Sequence

The amino acid sequence of a peptide prepared for HSV-2 type-specific detection can be confirmed by a number of well established methods. For example, the conventional method of Edman degradation can be used to determine the amino acid sequence of a peptide. Several variations of sequencing methods based on Edman degradation, including microsequencing, and methods based on mass spectrometry are also frequently used for this purpose.

E. Modification of Peptides

The peptides of the present invention can be modified to achieve more desirable properties. The design of chemically modified peptides and peptide mimics which are resistant to degradation by proteolytic enzymes or have improved solubility or binding ability is well known.

Modified amino acids or chemical derivatives of the peptides used for HSV-2 type-specific detection may contain additional chemical moieties of modified amino acids not normally a part of the glycoprotein G2. Covalent modifications of the peptide are within the scope of the present invention. Such modifications may be introduced into a peptide by reacting targeted amino acid residues of the peptide with an organic derivatizing agent that is capable of reacting with selected side chains or terminal residues. The following examples of chemical derivatives are provided by way of illustration and not by way of limitation.

The design of peptide mimics which are resistant to degradation by proteolytic enzymes is known to those skilled in the art. See e.g., Sawyer, *Structure-Based Drug Design*, P. Verapandia, Ed., N.Y. (1997); U.S. Pat. Nos. 5,552,534 and 5,550,251. Both peptide backbone and side chain modifications may be used in designing secondary structure mimicry. Possible modifications include substitution of D-amino acids, $N^{\alpha}$-Me-amino acids, $C_{\alpha}$-Me-amino acids, and dehydroamino acids. To this date, a variety of secondary structure mimetics have been designed and incorporated in peptides or peptidomimetics.

Other modifications include substitution of a natural amino acid with an unnatural hydroxylated amino acid, substitution of the carboxy groups in acidic amino acids with nitrile derivatives, substitution of the hydroxyl groups in basic amino acids with alkyl groups, or substitution of methionine with methionine sulfoxide. In addition, an amino acid of a peptide for type-specific detection of HSV-2 can be replaced by the same amino acid but of the opposite chirality, i.e., a naturally-occurring L-amino acid may be replaced by its D-configuration.

The peptides of the present invention can also be modified to enhance their ability to specifically bind to HSV-2 antibodies. For example, a linker, which may comprise a heterologous peptide, a heterologous protein, and/or chemicals of non-polypeptide in nature, may be introduced to either terminus of a peptide of the invention in order to facilitate the immobilization of the claimed peptide to a carrier, as well as to better present the peptide to HSV-2 antibodies. As another example, the peptides of the invention may be dimerized to achieve higher level of specific binding to HSV-2 antibodies. A variety of means can be used for dimerization, and the most commonly used method is through a disulfide bond. Since there is no naturally occurring cysteine residue in the peptides, a cysteine residue can be included as a part of the linker. The process of adding a linker to a peptide of the present invention will be discussed in detail in the next section.

IV. Immobilization of a Peptide to a Carrier

The peptides disclosed by the present invention for type-specific detection of HSV-2 antibodies are preferably immobilized to a solid support, or a carrier. A carrier is often a synthetic polymeric material, but may also be naturally-occurring. Examples of carrier material are acrylamide, cellulose, nitrocellulose, glass, polystyrene, polyethylene vinyl acetate, polypropylene, polymethacrylate, polyethylene, polysilicates, polyethylene oxide, polycarbonates, teflon, fluorocarbons, nylon, silicon rubber, collagen, polyanhydrides, polyglycolic acid, polylactic acid, polyorthoesters, polypropylfumarate, glycosaminoglycans, and polyamino acids. A carrier may be in one of the many useful forms including thin films or membranes, beads, bottles, dishes, fibers, woven fibers, shaped polymers, particles, and microparticles such as microspheres. Preferred forms of supports are plates and beads. The most preferred form of beads is magnetic beads or latex beads.

A. Attachment to a Linker

A peptide of the present invention can be attached to a carrier via various linkers. A linker can be attached to the N-or C-terminus of a peptide. In the case of indirect linkage between a peptide and a carrier, a linker may consist of a second peptide that is heterologous to the peptide of the invention, or may, in addition to a heterologous peptide, further comprise a protein heterologous to the peptide of the invention. Branched amino acid polymers can also be used as linkers, taking advantage of multiple functional groups on amino acid residues such as the two amine groups on a lysine residue. There are other suitable linkers well known to those of skill in the art, including but not limited to, straight or branched-chain carbon linkers, heterocyclic carbon linkers (e.g., SMCC), or polyether linkers. These linkers can be used in addition to or in place of a heterologous peptide and/or protein.

In the case of direct linkage, a linker can be a covalent bond (e.g., a disulfide bond) or a noncovalent bond (e.g., an ionic bond) between the peptide and the carrier.

1. Indirect Linkage

When the peptides of the present invention are obtained through synthetic means, heterologous peptides serving as linkers may be included at the time of peptide synthesis. For example, a linker consisting of one cysteine residue, one lysine residue, and at least two glycine residues can be included as a part of the peptide sequence to be synthesized, either at the N-or C-terminus. Other linkers such as straight or branched-chain carbon linkers, heterocyclic carbon linkers, or polyether linkers may also be used to join an HSV-2 peptide of the present invention alone or in combination with a heterologous peptide and/or protein. When a heterologous protein, such as BSA and KLH, is used in addition to a heterologous peptide in a linker, it may be joined to a peptide, to which a heterologous peptide is already added during synthesis, by chemical means following the synthesis and purification of the peptide. Such conjugation may be accomplished by joining the peptide and the heterologous protein through the α-carbon amino and carboxyl groups of the terminal amino acid residues, such as through a peptide bond; or by joining the amino acid residues of the peptide and the heterologous protein through their side groups, such as through a disulfide bond. Linkers such as heterologous peptides and/or proteins can also be joined to the HSV-2 peptides of the present invention through a functional group of an internal amino acid residue (e.g., a second carboxyl group of an aspartate residue) of the HSV-2 peptides.

When peptides of the present invention are obtained through recombinant means, a nucleotide sequence encoding a heterologous peptide or protein can be included during the subcloning process and the resulting recombinant polypeptide will thus already have a proper linker attached.

One skilled in the art will recognize that a variety of other linkers with appropriate functional groups such as carbon linkers or polyether linkers may also be useful to practice the present invention. These linkers may be joined to a peptide's constituent amino acids through their side groups (for example, through a disulfide linkage to cysteine). The linkers may also be joined to the α-carbon amino or carboxyl groups of the peptide's terminal amino acids.

2. Direct Linkage

The peptides of the present invention can be immobilized to a insoluble carrier directly. The strategies of attaching a peptide, which usually contains a variety of functional groups such as carboxylic acid (—COOH), free amine (—$NH_2$), or sulfhydryl (—SH) groups that are available for reaction with a suitable functional group on the carrier to result in a linkage, are similar to some approaches of attaching a peptide or protein linker to a carrier, the detailed discussion of which is provided in the next section.

B. Attachment to a Carrier

1. Covalent Bonds

The peptides for HSV-2 type-specific detection, with or without a linker, may be attached to a carrier via a covalent bond. Frequently, a carrier has some functional groups, such as amine, carboxylic acid, and sulfhydryl groups, with which the functional groups of a peptide or a linker may easily react and establish a covalent bond that conjugates the peptide and the carrier. A covalent bond joining a peptide of the present invention and a carrier can exist between the carrier and a terminal amino acid residue of the peptide, or between the carrier and an internal amino acid residue of the peptide. In case there is no functional group naturally present on a carrier suitable for this purpose, the carrier may be derivatized to expose or to attach additional reactive functional groups prior to conjugation. The derivatization may involve attachment of any of a number of molecules such as those available from Pierce Chemical Company, Rockford, Ill.

2. Non-covalent Bonds

Alternatively, a peptide can be linked to a carrier via the known interaction of a tag and a tag-binder. One of the partners of this binding interaction, e.g., a tag, can be attached to the peptide as a linker whereas the other partner, e.g., a tag binder, can be attached to the carrier. A number of tags and tag binders can be used, based upon known molecular interactions well described in the literature. For example, where a tag has a natural binder, e.g., biotin, it can be used in conjunction with appropriate tag binders (avidin, streptavidin, neutravidin, etc.) Receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors. In addition, some synthetic polymers, such as polyurethanes, polyesters, polycarbonates, polyureas, polyamides, polyethyleneimines, polyarylene sulfides, polysiloxanes, polyimides, and polyacetates can form an appropriate tag or tag binder as well.

A linker containing a tag can be attached to a peptide via a number of ways as described above. On the other hand, a tag binder can be fixed to a solid substrate (i.e., a carrier) using any of a variety of methods currently available. Solid substrates are commonly derivatized or functionalized by exposing all or a portion of the substrate to a chemical reagent which fixes a chemical group to the surface, and the chemical group is in turn reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:6031-6040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

V. Assays for Type-Specific HSV-2 Antibody Detection

A. Detection of HSV-2 Antibodies Using Peptides of the Present Invention

In order for peptides of the present invention to be useful for HSV-2 type-specific detection, they must first be able to bind HSV-2 antibodies with specificity. To test such specific binding, a number of well known immunological binding assays can be performed. See, e.g., U.S. Pat. Nos. 4,366,241; 4,376,110; 4,517,288; and 4,837,168. For a general review of immunoassay methods, see also Asai, *Methods in Cell Biology*, Volume 37: *Antibodies in Cell Biology*, Academic Press, Inc. NY (1993).

Typically, peptides of the present invention can be immobilized and used as a so-called "capture agent" for HSV-2 antibodies. Samples that are known to contain HSV-2 antibodies but not HSV-1 antibodies may be used in binding assays to screen for peptides that can bind HSV-2 antibodies with specificity. The proper binding conditions are well known in the art and general instructions on performing such binding assays may be found in many scientific publications. See, e.g., Harlow and Lane, *Antibodies: A Laboratory Manual*, Cold Spring Harbor Laboratory (1988). Upon formation of the antibody-peptide complex, a labeling agent is used to indicate the presence of such complex. In the present case, there are several ways of using a labeling agent for this purpose. For instance, the labeling agent may be a second antibody that can recognize an antibody-peptide complex and bears a label. Alternatively, the second antibody may itself lack a label, but can in turn be bound by a labeled third antibody specific to antibodies of the species from which the second antibody is derived. The second antibody may also be modified with a detectable moiety, such as biotin, to which a third labeled molecule can bind with specificity, such as streptavidin with a label. In addition, other proteins capable of specifically binding immnunoglobulin constant regions, such as protein A or protein G, can also be used as labeling agents. These proteins are normal constituents of streptococcal bacteria cell walls, and exhibit a strong non-immunogenic reactivity toward immunoglobulin constant regions from a variety of species. See, generally, Kronval et al., *J Immunol.*, 111:1401-1406 (1973); and Akerstrom et al., *J. Immunol.*, 135:2589-2592 (1985).

Throughout the assays, incubation and/or washing steps may be required after each combination of reagents. Incubation steps can vary from about 5 seconds to several hours, preferably from about 5 minutes to about 24 hours. The incubation time will vary, depending upon the assay format, particular peptides, volume of solution, concentrations, and the like. The assays are frequently carried out at ambient temperature, although they can be conducted over a range of temperatures, such as from about 10° C. to about 40° C.

Different means of labeling can be used for detection of antibody-peptide complex. A labeling moiety can be, e.g., a fluorescent molecule (such as fluorescein, rhodamine, Texas Red, and phycoerythrin) or an enzyme molecule (such as horseradish peroxidase, alkaline phosphatase, and β-galactosidase) attached to a second or a third antibody, allowing detection based on fluorescence emission or a product of a chemical reaction catalyzed by the enzyme. Radioactive labels involving various isotopes, such as $^3$H, $^{125}$I, $^{35}$S, $^{14}$C, or $^{32}$P, can also be attached to appropriate molecules, and detection of antibody-peptide complex can thus be made by any suitable methods that registers radioactivity, such as autoradiography. See, e.g., Tijssen, *"Practice and Theory of Enzyme Immunoassays," Laboratory Techniques in Biochemistry and Molecular Biology*, Burdon and van Knippenberg Eds., Elsevier (1985), pp. 9-20. An introduction to labels, labeling procedures, and detection of labels can also be found in Polak and Van Noorden, *Introduction to Immunocytochemistry*, 2d Ed., Springer Verlag, NY (1997); and in Haugland, *Handbook of Fluorescent Probes and Research Chemicals*, a combined handbook and catalogue published by Molecular Probes, Inc. (1996).

B. Flow Cytometry

Flow cytometry is one of the preferred methods for detecting the presence of HSV-2 type-specific antibodies, where the peptides of the present invention are conjugated to suitable particles and specific binding of HSV-2 antibodies is detected through the binding of a third molecule labeled with, e.g., fluorescence. Methods of and instrumentation for flow cytometry are known in the art, and can be used in the practice of the present invention. Flow cytometry in general resides in the passage of a suspension of the microparticles as a stream past a laser beam and the detection of fluorescent emission from each particle by a photo multiplier tube. Detailed descriptions of instrumentation and methods for flow cytometry are found in the literature. Examples are McHugh, "Flow Microsphere Irnmunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays," *Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory*, 185-189 (Liss 1979); Wilson et al., "A New Microsphere-Based Immunofluorescence Assay Using Flow Cytometry," *J. Immunol. Meth.* 107: 225-230 (1988); Fulwyler et al., "Flow Microsphere Immunoassay for the Quantitative and Simultaneous Detection of Multiple Soluble Analytes," *Meth. Cell Biol.* 33: 613-629 (1990); Coulter Electronics Inc., United Kingdom Patent No. 1,561,042 (published Feb. 13, 1980); and Steinkamp et al., *Review of Scientific Instruments* 44(9): 1301-1310 (1973).

The particles used in the practice of this invention are preferably microscopic in size and formed of a polymeric material. Polymers that will be useful as microparticles are those that are chemically inert relative to the components of the biological sample and to the assay reagents other than the binding member coatings that are affixed to the microparticle surface. Suitable microparticle materials will also have minimal autofluorescence, will be solid and insoluble in the sample and in any buffers, solvents, carriers, diluents, or suspending agents used in the assay, and will be capable of affixing to the appropriate coating material, preferably through covalent bonding. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. The size range of the microparticles can vary and particular size ranges are not critical to the invention. In most cases, the microparticles will range in diameter from about 0.5 micrometers to about 100 micrometers, and preferably from about 0.3 micrometers to about 40 micrometers.

To facilitate the particle recovery and washing steps of the assay, the particles preferably contain a magnetically responsive material, i.e., any material that responds to a magnetic field. Separation of the solid and liquid phases, either after incubation or after a washing step, is then achieved by imposing a magnetic field on the reaction vessel in which the suspension is incubated, causing the particles to adhere to the wall of the vessel and thereby permitting the liquid to be removed by decantation or aspiration. Magnetically responsive materials of interest in this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, $CoO$, $NiO$, $Mn_2O_3$, $Cr_2O_3$, and $CoMnP$.

The magnetically responsive material can be dispersed throughout the polymer, applied as a coating on the polymer surface or as one of two or more coatings on the surface, or incorporated or affixed in any other manner that secures the material in to the particle. The quantity of magnetically responsive material in the particle is not critical and can vary over a wide range. The quantity can affect the density of the microparticle, however, and both the quantity and the particle size can affect the ease of maintaining the microparticle in suspension for purposes of achieving maximal contact between the liquid and solid phase and for facilitating flow cytometry. An excessive quantity of magnetically responsive material in the microparticles may produce autofluorescence at a level high enough to interfere with the assay results. It is therefore preferred that the concentration of magnetically responsive material be low enough to minimize any autofluorescence emanating from the material. With these considerations in mind, the magnetically responsive material in a particle in accordance with this invention preferably ranges from about 0.05% to about 75% by weight of the particle as a whole. A more preferred weight percent range is from about 1% to about 50%, a still more preferred weight percent range is from about 2% to about 25%, and an even more preferred weight percent range is from about 2% to about 8%.

Coating of the particle surface with the appropriate assay reagent can be achieved by electrostatic attraction, specific affinity interaction, hydrophobic interaction, or covalent bonding. Covalent bonding is preferred. The polymer can be derivatized with functional groups for covalent attachment of the assay reagent by conventional means, notably by the use of monomers that contain the functional groups, such monomers serving either as the sole monomer or as a co-monomer. Examples of suitable functional groups are amine groups (—$NH_2$), ammonium groups (—$NH_3^+$ or —$NR_3^+$), hydroxyl groups (—OH), carboxylic acid groups (—COOH), and isocyanate groups (—NCO). Useful monomers for introducing carboxylic acid groups into polyolefins, for example, are acrylic acid and methacrylic acid.

Linkers can be used as a means of increasing the density of antibody-recognizable epitopes on the particle surface and decreasing steric hindrance. This will increase the range and sensitivity of the assay. Linkers can also be used as a means of adding specific types of reactive groups to the solid phase surface if needed to secure the particular coating materials of this invention. Examples of suitable useful functional groups are polylysine, polyaspartic acid, polyglutamic acid, and polyarginine.

In general, care should be taken to avoid the use of particles that exhibit high autofluorescence. Particles formed by conventional emulsion polymerization techniques from a wide variety of starting monomers are generally suitable since they exhibit at most a low level of autofluorescence. Conversely, particles that have been modified to increase their porosity and hence their surface area, i.e., those particles that are referred to in the literature as "macroporous" particles, are less desirable since they tend to exhibit high autofluorescence. A further consideration is that autofluorescence increases with increasing size and increasing percentage of divinylbenzene monomer.

The labels used in the labeled binding members may be any label that is capable of emitting detectable signal. Preferred such labels are fluorophores. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

The following is a list of examples of fluorophores:
4-acetamido-4'-isothiocyanatostilbene-2,2' disulfonic acid
acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin
7-amino-4-methylcoumarin (AMC, Coumarin 120)
7-amino-4-trifluoromethylcoumarin (Coumarin 151)
cyanine dyes
cyanosine
4', 6-diaminidino-2-phenylindole (DAPI)
5', 5"-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin
eosin isothiocyanate
erythrosin B
erythrosin isothiocyanate
ethidium
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
fluorescamine
IR144
IR1446
Malachite Green isothiocyanate
4-methylumbelliferone
ortho cresolphthalein
nitrotyrosine
pararosaniline
PhenolRed
Phycobiliproteins (B-phycoerythrin, R-phycoerythrin, etc)
o-phthaldialdehyde
pyrene
pyrene butyrate
succinimidyl 1-pyrene butyrate
quantum dots
Reactive Red 4 (Cibacron™Brilliant Red 3B-A)
6-carboxy-X-rhodamine (ROX)
6-carboxyrhodamine (R6G)
lissamine rhodamine B sulfonyl chloride rhodamine (Rhod)
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
lanthanide chelate derivatives The attachment of any of these fluorophores to the binding molecules described above to form assay reagents for use in the practice of this invention is achieved by conventional covalent bonding, using appropriate functional groups on the fluorophores and on the binding members. The recognition of such groups and the reactions to form the linkages will be readily apparent to those skilled in the art.

Similarly, methods of and instrumentation for applying and removing a magnetic field as part of an automated assay are known to those skilled in the art and reported in the literature. Examples of literature reports are Forrest et al., U.S. Pat. No. 4,141,687 (Technicon Instruments Corporation, Feb. 27, 1979); Ithakissios, U.S. Pat. No. 4,115,534 (Minnesota Mining and Manufacturing Company, Sep. 19, 1978); Vlieger, A.M., et al., *Analytical Biochemistry* 205:1-7 (1992); Dudley, *Journal of Clinical Immunoassay* 14:77-82 (1991); and Smart, *Journal of Clinical Immunoassay* 15:246-251 (1992). All of the citations in this and the preceding paragraph are incorporated herein by reference.

C. Non-Reactivity to HSV-1 Antibodies by Peptides of the Present Invention

Another equally important aspect of the necessary characteristics of peptides to be used for HSV-2 type-specific detection is that they must not bind HSV-1 antibodies with detectable specificity, particularly in the test formats used for HSV-2 antibody detection. Once peptides are shown to react to HSV-2 antibodies specifically, they will be further tested for any possible cross-reactivity to HSV-1 antibodies and antibodies against other viruses such as the herpes family. To test their non-reactivity to HSV-1 antibodies, the peptides are immobilized and used as “capture agents” in immunoassays essentially identical to those described in last section, except that samples confirmed to contain HSV-1 antibodies (but not HSV-2 antibodies) are used for the binding assays.

The following examples are provided for the purpose of illustration and not limitation.

EXAMPLES

I. Peptide Synthesis

Peptides listed in Table 1 were synthesized as monomers using the N-α-protecting group Boc or Fmoc.

PBS. The first peak was collected and the protein concentration was estimated by absorbance at 280 nm.

The monomer peptide (1 mg) was mixed with 1 mg of the modified BSA and stored at 4° C. overnight. The peptide-BSA conjugate was purified through size exclusion chromatography.

IV. Preparation of a Dimer Peptide-BSA Conjugate

A dimer peptide-BSA conjugate can be prepared in accordance with the following description.

1. SMCC-Peptide Dimer

50 µl of SMCC solution in DMSO (10 mg/ml) is added to 1 ml of peptide dimer solution (5 mg/ml) in 100 mM phosphate (pH 8.0). After incubation for 2 hours, the modified peptide is purified by HPLC chromatography.

2. 2-Mercaptoacetyl-BSA

50 µl of N-succinimidyl S-acetylthioacetate (SATA) (10 mg/ml) in DMSO is added to 1 ml of BSA (10 mg/ml) in 100 mM phosphate (pH 8.0). After incubation for 2 hours, 100 µl of 200 mM N-ethyl maleimide containing 10 mM EDTA is added. The reaction mixture is incubated at room temperature for 1 hour and then applied to a Sephadex G-25 column. The modified BSA is eluted from the column with 10 mM PBS.

3. Peptide Dimer-BSA Conjugate 4 mg of the modified BSA is mixed with 4 mg modified peptide at 2-8° C. and the mixture is incubated overnight. The conjugated peptide is purified by size exclusion chromatography.

TABLE 1 gG-2 Peptides Synthesized

| Name | SEQ ID NO: | | | | | Sequence | | | | |
|---|---|---|---|---|---|---|---|---|---|---|
| 1 | 9 | | | PGSPAPPP | PEHRGG | PEEFEGAGDG | EPPEDDDS | ATGL | GG | CK |
| 2 | 10 | | | APPP | PEHRGG | PEEFEGAGDG | EPPEDDDS | | GGGG | CK |
| 3 | 11 | | | | PEHRGG | PEEFEGAGDG | EPPEDDDS | | GGGG | CK |
| 4 | 12 | | | | | PEEFEGAGDG | EPPEDDDS | | GGGG | CK |
| 5 | 8 | KC | GGGG | | PEHRGG | PEEFEGAGDG | EPPEDDDS | | | |
| 6 | 13 | | | | RGRAG | RRRYAHPSVR | | | GGGG | CK |
| 7 | 14 | | | | WRGRAG | RRRYAHPSVR | Y | | GGGG | CK |
| 8 | 15 | | | | RGRAG | RRRYAHPSVR | YVCLPPER | D | GGGG | CK |
| 9 | 16 | | | | | RRRYAHPSVR | YVCLPPER | D | GGGG | CK |
| 10 | 17 | KC | GGGG | | WRGRAG | RRRYAHPSVR | Y | | | |
| 11 | 18 | KC | GGGG | | RGRAG | RRRYAHPSVR | | | | |
| 12 | — | | | | (PEHRGG | PEEFEGAGDG | EPPEDDDS | | GGGG) 4K3 | CK |
| 13 | — | | | | (WRGRAG | RRRYAHPSVR | Y | | GGGG) 4K3 | CK |

II. Dimerization

An optional step of peptide dimerization is performed as follows: a monomer peptide was dissolved in either deionized water or 0.1 M sodium bicarbonate and stirred at 4° C. overnight. The resulting oxidized, dimeric peptide was purified by preparative HPLC using a C18 column.

III. Preparation of a Monomer Peptide-BSA conjugate

To a solution of Bovine Serum Albumin (BSA) in 0.1 mM borate buffer (pH8.0) (10 mg/ml), 154 µl of SMCC, N-hydroxysuccimide in dimethylsulfoxide (DMSO) was added. The mixture was incubated at room temperature for 2 hours, applied to a Sephadex G-25 column (30 ml) pre-equilibrated with 10 mM phosphate-saline (PBS, pH7.4) and eluted with

V. Preparation of Peptide or Peptide-BSA Coated Magnetic Beads

To 6 mg of magnetic beads washed with 25 mM 2-[N-morpholino]ethanesulfonic acid (MES) (pH6.1) twice 588 µl of deionized water, 80 µl of 0.5 M MES (pH6.1), 92 µl of 100 mg/ml N-hydroxysuccinimide (NHS) and 40 µl of 50 mg/ml 1-ethyl -3-(3-dimethylaminopropyl)carbodiimide (EDC) in deionized water were added and the mixture was vortexed at room temperature for 30 minutes. The activated beads were washed twice with 25 mM MES (pH6.1). Subsequently, 100 µl of 0.5 M MES (pH 6.1), 720 µl of deionized water, and 180 µl of Peptide (1 mg/ml) or Peptide-BSA conjugate (1 mg/ml) were added and the mixture vortexed. The mixture was further incubated at room temperature on a rotator for 2 hours and centrifuged at 7000 rpm for 2 min. One ml of 1% BSA in PBS containing 20 mM Tris Base was added after discarding the supernatant, mixed for 2 hour at room temperature on a rotator and then centrifuged to remove the supernatant. The beads were washed with 1% BSA in 10 mM PBS twice and stored in 1 ml of 1% BSA. Scheme 1 in FIG. 6 shows an illustrative process of conjugating an HSV-2 peptide via a heterologous peptide already attached at its C-terminus to SMCC, which is in turn attached to a microsphere via BSA.

VI. Flow Cytometry Immunoassay (FCIA)

The peptides or peptide-BSA conjugates, such as those in Table 1, were coupled to predefined magnetic beads (every peptide or peptide-BSA conjugate was coupled to magnetic beads whose fluorescence is characteristic of a particular region of dye content) and were mixed together at similar bead number for each region of magnetic beads. The mixed beads were diluted with 1% BSA in PBS with 0.1% Tween 20 to 1000 copies of each region magnetic beads per ml.

To a microtiter tube 100 μl of sample diluent, 5 μl of patient sample and 100 μl of the bead mix were added and incubated at 37° C. on a shaker for 20 minutes. After magnetic separation, the beads were washed with wash buffer (10 mM PBS with 0.1% Tween 20) twice. 50 μl of antihuman IgG (Fc specific)-B-phycoerythrin conjugate was added. Following a 10-minute incubation on a shaker at 37° C., the beads were washed again with the wash buffer twice and resuspended in 50 μl of the wash buffer. The beads were counted and analyzed on Luminex 100 instrument. The amount of antibodies (IgG) bound to the magnetic beads was determined with antihuman IgG conjugated to phycoerythrin.

VII. Comparison with Commercially Available Assay Systems

Studies using 137 clinically defined patient samples have demonstrated that the assay system using the peptide-BSA conjugates of the present invention performed better than the commercially available gG-2 based HSV-2 type-specific IgG assay systems and had a 100% agreement with the confirmation test of Western Blot assays (Table 2).

TABLE 2

Peptide-Based HSV-2 Type-Specific Assay

Peptide-Based HSV-2 IgG Assay

|  | Agreement | Sensitivity | Specificity |
|---|---|---|---|
| Meridian EIA | 93.10% | 86.20% | 96.60% |
| MRL EIA | 97.60% | 93.10% | 100% |
| Western Blot | 100% | 100% | 100% |

VIII. Non-reactivity to HSV-1 IgG

HSV-2 type-specific immunoassay systems of the present invention are tested for lack of cross-reactivity to antibodies against other viruses of the herpes family, particulary HSV-1. Table 3 demonstrates the lack of cross-reactivity to HSV-1 IgG as confirmed by two commercially available HSV-2 type-specific assay systems and Western Blot assays.

TABLE 3

Non-Reactivity to HSV-1 Antibody Positive Samples

| Sample I.D. | Meridian HSV-1 Value | Meridian HSV-1 Result | Meridian HSV-2 Value | Meridian HSV-2 Result | MRL HSV-1 Value | MRL HSV-1 Result | MRL HSV-2 Value | MRL HSV-2 Result | Western Blot HSV-1 Result | Western Blot HSV-2 Result | Present Method HSV-2 Value | Present Method HSV-2 Result |
|---|---|---|---|---|---|---|---|---|---|---|---|---|
| 64 | 1.40 | Pos | 0.13 | Neg | 1.62 | Pos | 0.11 | Neg | Pos | Neg | 0.08 | Neg |
| 92 | 1.42 | Pos | 0.11 | Neg | 3.17 | Pos | 0.05 | Neg | Pos | Neg | 0.06 | Neg |
| 66 | 1.43 | Pos | 0.55 | Neg | 1.46 | Pos | 0.16 | Neg | Pos | Neg | 0.09 | Neg |
| 63 | 1.44 | Pos | 0.40 | Neg | 1.79 | Pos | 0.04 | Neg | Pos | Neg | 0.07 | Neg |
| 110 | 1.57 | Pos | 0.41 | Neg | 2.11 | Pos | 0.61 | Neg | Pos | Neg | 0.79 | Neg |
| 114 | 1.61 | Pos | 0.10 | Neg | 2.01 | Pos | 0.15 | Neg | Pos | Neg | 0.09 | Neg |
| 43 | 1.66 | Pos | 0.06 | Neg | 2.44 | Pos | 0.05 | Neg | Pos | Neg | 0.07 | Neg |
| 67 | 1.70 | Pos | 0.15 | Neg | 2.37 | Pos | 0.20 | Neg | Pos | Neg | 0.10 | Neg |
| 36 | 1.90 | Pos | 0.14 | Neg | 2.78 | Pos | 0.28 | Neg | Pos | Neg | 0.08 | Neg |
| 101 | 2.04 | Pos | 0.13 | Neg | 2.48 | Pos | 0.26 | Neg | Pos | Neg | 0.13 | Neg |
| 46 | 2.08 | Pos | 0.10 | Neg | 3.54 | Pos | 0.15 | Neg | Pos | Neg | 0.08 | Neg |
| 29 | 2.27 | Pos | 2.03 | Pos | 0.39 | Neg | 0.15 | Neg |  |  | 0.06 | Neg |
| 61 | 2.47 | Pos | 2.95 | Pos | 0.90 | Equ | 0.30 | Neg |  |  | 0.12 | Neg |
| 11 | 2.78 | Pos | 1.20 | Neg | 4.36 | Pos | 8.72 | Pos |  |  | 0.87 | Neg |
| 56 | 2.79 | Pos | 0.19 | Neg | 3.78 | Pos | 0.07 | Neg | Pos | Neg | 0.10 | Neg |
| 106 | 2.89 | Pos | 0.07 | Neg | 4.82 | Pos | 0.38 | Neg | Pos | Neg | 0.11 | Neg |
| 12 | 3.72 | Pos | 0.15 | Neg | 5.79 | Pos | 0.95 | Equ | Pos | Neg | 0.09 | Neg |
| 78 | 3.96 | Pos | 0.19 | Neg | 5.91 | Pos | 0.25 | Neg | Pos | Neg | 0.10 | Neg |
| 6 | 4.26 | Pos | 0.24 | Neg | 9.25 | Pos | 0.10 | Neg | Pos | Neg | 0.10 | Neg |
| 18 | 4.46 | Pos | 0.57 | Neg | 8.22 | Pos | 0.17 | Neg | Pos | Neg | 0.09 | Neg |
| 13 | 4.70 | Pos | 0.05 | Neg | 6.68 | Pos | 0.10 | Neg | Pos | Neg | 0.05 | Neg |
| 2 | 4.93 | Pos | 0.22 | Neg | 9.25 | Pos | 0.47 | Neg | Pos | Neg | 0.09 | Neg |
| 10 | 4.99 | Pos | 0.18 | Neg | 7.82 | Pos | 0.13 | Neg | Pos | Neg | 0.08 | Neg |
| 93 | 5.05 | Pos | 1.83 | Pos | 0.36 | Neg | 0.18 | Neg |  |  | 0.14 | Neg |
| 20 | 5.14 | Pos | 0.10 | Neg | 7.02 | Pos | 0.40 | Neg | Pos | Neg | 0.06 | Neg |
| 21 | 5.27 | Pos | 0.09 | Neg | 6.95 | Pos | 0.10 | Neg | Pos | Neg | 0.09 | Neg |
| 59 | 5.63 | Pos | 0.28 | Neg | 9.25 | Pos | 0.72 | Neg | Pos | Neg | 0.11 | Neg |
| 88 | 5.79 | Pos | 0.13 | Neg | 6.93 | Pos | 0.08 | Neg | Pos | Neg | 0.08 | Neg |
| 44 | 6.08 | Pos | 0.19 | Neg | 8.55 | Pos | 0.33 | Neg | Pos | Neg | 0.12 | Neg |
| 62 | 6.16 | Pos | 0.12 | Neg | 9.25 | Pos | 0.24 | Neg | Pos | Neg | 0.09 | Neg |
| 83 | 6.25 | Pos | 0.10 | Neg | 7.96 | Pos | 0.15 | Neg | Pos | Neg | 0.06 | Neg |

TABLE 3-continued

Non-Reactivity to HSV-1 Antibody Positive Samples

| Sample I.D. | Meridian | | | | MRL | | | | Western Blot | | Present Method | |
|---|---|---|---|---|---|---|---|---|---|---|---|---|
| | HSV-1 | | HSV-2 | | HSV-1 | | HSV-2 | | HSV-1 | HSV-2 | HSV-2 | |
| | Value | Result | Value | Result | Value | Result | Value | Result | Result | Result | Value | Result |
| 45  | 6.54 | Pos | 0.11 | Neg | 9.25 | Pos | 0.44 | Neg | Pos | Neg | 0.42 | Neg |
| 51  | 6.55 | Pos | 0.11 | Neg | 9.25 | Pos | 0.08 | Neg | Pos | Neg | 0.06 | Neg |
| 7   | 6.56 | Pos | 0.16 | Neg | 9.25 | Pos | 0.15 | Neg | Pos | Neg | 0.10 | Neg |
| 25  | 6.56 | Pos | 0.14 | Neg | 9.25 | Pos | 0.12 | Neg | Pos | Neg | 0.08 | Neg |
| 27  | 6.56 | Pos | 0.13 | Neg | 8.85 | Pos | 0.41 | Neg | Pos | Neg | 0.14 | Neg |
| 40  | 6.56 | Pos | 0.20 | Neg | 9.25 | Pos | 0.49 | Neg | Pos | Neg | 0.22 | Neg |
| 41  | 6.56 | Pos | 0.34 | Neg | 9.25 | Pos | 0.19 | Neg | Pos | Neg | 0.15 | Neg |
| 50  | 6.56 | Pos | 0.15 | Neg | 9.25 | Pos | 0.07 | Neg | Pos | Neg | 0.08 | Neg |
| 58  | 6.56 | Pos | 0.73 | Neg | 8.45 | Pos | 0.24 | Neg | Pos | Neg | 0.10 | Neg |
| 74  | 6.56 | Pos | 0.14 | Neg | 9.25 | Pos | 0.09 | Neg | Pos | Neg | 0.09 | Neg |
| 75  | 6.56 | Pos | 0.15 | Neg | 8.78 | Pos | 0.17 | Neg | Pos | Neg | 0.07 | Neg |
| 77  | 6.56 | Pos | 0.11 | Neg | 8.42 | Pos | 0.22 | Neg | Pos | Neg | 0.41 | Neg |
| 80  | 6.56 | Pos | 0.58 | Neg | 8.05 | Pos | 0.98 | Equ | Pos | Neg | 0.89 | Neg |
| 85  | 6.56 | Pos | 0.12 | Neg | 8.88 | Pos | 0.42 | Neg | Pos | Neg | 0.09 | Neg |
| 100 | 8.46 | Pos | 0.07 | Neg | 9.25 | Pos | 0.08 | Neg | Pos | Neg | 0.07 | Neg |
| 118 | 8.46 | Pos | 0.08 | Neg | 9.06 | Pos | 0.45 | Neg | Pos | Neg | 0.07 | Neg |
| 54  | 1.53 | Pos | 3.30 | Pos | 3.15 | Pos | 6.79 | Pos | | | 5.77 | Pos |
| 52  | 6.46 | Pos | 2.03 | Pos | 9.25 | Pos | 6.47 | Pos | | | 2.59 | Pos |
| 24  | 6.56 | Pos | 2.09 | Pos | 6.62 | Pos | 8.72 | Pos | | | 5.53 | Pos |
| 37  | 6.56 | Pos | 2.78 | Pos | 9.25 | Pos | 6.73 | Pos | | | 2.17 | Pos |
| 42  | 6.56 | Pos | 5.85 | Pos | 9.25 | Pos | 8.72 | Pos | | | 6.41 | Pos |
| 57  | 6.56 | Pos | 4.28 | Pos | 9.14 | Pos | 5.54 | Pos | | | 4.43 | Pos |

What is claimed is:

1. A composition comprising a purified HSV-2 peptide, wherein the peptide consists of amino acids 5 to 32 of SEQ ID NO:1, amino acids 9 to 32 of SEQ ID NO:1, or SEQ ID NO:1.

2. The composition of claim 1, wherein the peptide consists of amino acids 5 to 32 of SEQ ID NO:1.

3. The composition of claim 1, wherein the peptide consists of amino acids 9 to 32 of SEQ ID NO:1.

4. The composition of claim 1, wherein the peptide consists of SEQ ID NO:1.

5. The composition of claim 1, wherein the peptide is dimerized.

6. The composition of claim 5, wherein the peptide is dimerized via a linker that provides a disulfide bond.

7. The composition of claim 1, wherein the peptide is linked to a carrier.

8. The composition of claim 7, wherein the carrier is a carboxylated microsphere.

9. The composition of claim 8, wherein the microsphere is a latex or magnetic microsphere.

10. The composition of claim 7, wherein the peptide is linked to the carrier via a heterologous linker at the N-terminus or the C-terminus of the peptide.

11. The composition of claim 7, wherein the peptide is linked to the carrier via a heterologous linker at an internal amino acid residue of the peptide.

12. The composition of claim 10, wherein the linker comprises a heterologous peptide.

13. The composition of claim 10, wherein the linker consists of a heterologous protein.

14. The composition of claim 12, wherein the linker further comprises a heterologous protein.

15. The composition of claim 14, wherein the heterologous protein is bovine serum albumin (BSA).

16. The composition of claim 14, wherein the heterologous protein is Keyhole Limpet Hemocyanin (KLH).

17. The composition of claim 12, wherein the linker consists of a heterologous peptide.

18. The composition of claim 12, wherein the heterologous peptide comprises one cysteine residue, one lysine residue, and at least two glycine residues.

19. The composition of claim 10, wherein the linker comprises a branched amino acid polymer.

20. The composition of claim 19, wherein the branched amino acid polymer comprises the structure of:

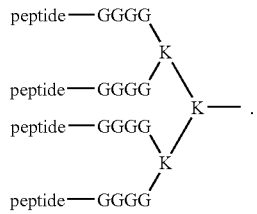

21. The composition of claim 12, wherein
(1) the peptide consists of SEQ ID NO:1;
(2) the carrier is a carboxylated magnetic microsphere;
(3) the linker further comprises 4-(maleimidomethyl)-1-cyclohexanecarboxylic acid (SMCC) and a heterologous peptide consists of the amino acid sequence GGCK (SEQ ID NO:2); and
(4) the heterologous peptide is attached to the peptide at the C-terminus of the peptide.

22. The composition of claim 21, wherein the linker further comprises the heterologous protein BSA, which is directly attached to the carrier, and wherein SMCC is attached (i) to BSA and (ii) via the heterologous peptide to the peptide.

23. The composition of claim 12, wherein
(1) the peptide consists of amino acids 5 to 32 of SEQ ID NO:1;
(2) the carrier is a carboxylated magnetic microsphere;
(3) the linker further comprises SMCC and a heterologous peptide consists of the amino acid sequence GGGGCK (SEQ ID NO:3); and
(4) the heterologous peptide is attached to the peptide at the C-terminus of the peptide.

24. The composition of claim 23, wherein the linker further comprises a heterologous protein BSA, which is directly attached to the carrier, and wherein SMCC is attached (i) to BSA and (ii) via the heterologous peptide to the peptide.

25. The composition of claim 12, wherein
(1) the peptide consists of amino acids 9 to 32 of SEQ ID NO:1;
(2) the carrier is a carboxylated magnetic microsphere;
(3) the linker further comprises SMCC and a heterologous peptide consists of the amino acid sequence GGGGCK (SEQ ID NO:3); and
(4) the heterologous peptide is attached to the peptide at the C-terminus of the peptide.

26. The composition of claim 25, wherein the linker further comprises the heterologous protein BSA, which is directly attached to the carrier, and wherein SMCC is attached (i) to BSA and (ii) via the heterologous peptide to the peptide.

27. The composition of claim 12, wherein
(1) the peptide consists of amino acids 9 to 32 of SEQ ID NO:1;
(2) the carrier is a carboxylated magnetic microsphere;
(3) the linker further comprises SMCC and the heterologous peptide consists of the amino acid sequence KCGGGG (SEQ ID NO:4); and
(4) the heterologous peptide is attached to the peptide at the N-terminus of the peptide.

28. The composition of claim 27, wherein the linker further comprises a heterologous protein BSA, which is directly attached to the carrier, and wherein SMCC is attached (i) to BSA and (ii) via the heterologous peptide to the peptide.

29. The composition of claim 20, wherein
(1) the peptide consists of amino acids 9 to 32 of SEQ ID NO:1;
(2) the carrier is a carboxylated microsphere; and
(3) the branched amino acid polymer further comprises the short peptide of CK cysteine-lysine), wherein the short peptide via its C (cysteine) residue is directly attached to the last K residue of the branched amino acid polymer.

30. A method for specific detection of HSV-2 antibodies in a biological sample, comprising the steps of:
(a) contacting the biological sample with a composition of claim 1; and
(b) detecting whether antigen-antibody binding has occurred between the peptide and an antibody component of the biological sample, in which the detection of antigen-antibody binding indicates the presence of HSV-2 antibodies in the biological sample.

31. The method of claim 30, wherein the peptide is conjugated to a suitable particle, and wherein step (b) is performed by flow cytometry.

32. The method of claim 30, wherein the biological sample is whole blood, serum, plasma, cerebrospinal fluid, vesicle fluid, or mucus.

33. The method of claim 30, wherein the peptide consists of amino acids 5 to 32 of SEQ ID NO:1.

34. The method of claim 30, wherein the peptide consists of amino acids 9 to 32 of SEQ ID NO:1.

35. The method of claim 30, wherein the peptide consists of SEQ ID NO:1.

36. The method of claim 30, wherein the peptide is linked to a carrier.

37. The method of claim 36, wherein the carrier is a carboxylated microsphere.

38. The method of claim 37, wherein the microsphere is a latex or magnetic microsphere.

39. The method of claim 30, wherein the peptide is dimerized.

40. The method of claim 39, wherein the peptide is dimerized via a linker that provides a disulfide bond.

41. The method of claim 36, wherein the peptide is linked to the carrier via a heterologous linker at the N-terminus or the C-terminus of the peptide.

42. The method of claim 36, wherein the peptide is linked to the carrier via a heterologous linker at an internal amino acid residue of the peptide.

43. The method of claim 41, wherein the linker comprises a heterologous peptide.

44. The method of claim 41, wherein the linker consists of a heterologous protein.

45. The method of claim 43, wherein the linker further comprises a heterologous protein.

46. The method of claim 45, wherein the heterologous protein is BSA.

47. The method of claim 45, wherein the heterologous protein is KLH.

48. The method of claim 43, wherein the linker consists of a heterologous peptide.

49. The method of claim 43, wherein the heterologous peptide comprises one cysteine residue, one lysine residue, and at least two glycine residues.

50. The method of claim 41, wherein the linker comprises a branched amino acid polymer.

51. The method of claim 50, wherein the linker comprises the structure of:

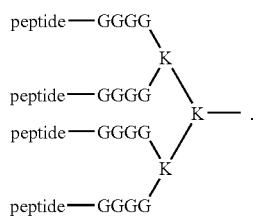

52. The method of claim 43, wherein
(1) the peptide consists of SEQ ID NO:1;
(2) the carrier is a carboxylated magnetic microsphere;
(3) the linker comprises SMCC and a heterologous peptide consists of the amino acid sequence GGCK (SEQ ID NO:2);
(4) the heterologous peptide is attached to the peptide at the C-terminus of the peptide; and
(5) step (b) is performed by flow cytometry.

53. The method of claim 52, wherein the linker further comprises the heterologous protein BSA, which is directly attached to the carrier, and wherein SMCC is attached (i) to BSA and (ii) via the heterologous peptide to the peptide.

54. The method of claim 43, wherein
(1) the peptide consists of amino acids 5 to 32 of of SEQ ID NO:1;
(2) the carrier is a carboxylated magnetic microsphere;
(3) the linker comprises SMCC and the heterologous peptide consists of the amino acid sequence GGGGCK (SEQ ID NO: 3);
(4) the heterologous peptide is attached to the peptide at the C-terminus of the peptide; and
(5) step (b) is performed by flow cytometry.

55. The method of claim 54, wherein the linker further comprises the heterologous protein BSA, which is directly attached to the carrier, and wherein SMCC is attached (i) to BSA and (ii) via the heterologous peptide to the peptide.

56. The method of claim 43, wherein
(1) the peptide consists of 9 to 32 amino acids of of SEQ ID NO:1;
(2) the carrier is a carboxylated magnetic microsphere;
(3) the linker comprises SMCC and a heterologous peptide consists of the amino acid sequence GGGGCK (SEQ ID NO:3);
(4) the heterologous peptide is attached to the peptide at the C-terminus of the peptide; and
(5) step (b) is performed by flow cytometry.

57. The method of claim 56, wherein the linker further comprises the heterologous protein BSA, which is directly attached to the carrier, and wherein SMCC is attached (i) to BSA and (ii) via the heterologous peptide to the peptide.

58. The method of claim 43, wherein
(1) the peptide consists of amino acid sequence consisting of amino acids 9 to 32 of SEQ ID NO:1;
(2) the carrier is a carboxylated magnetic microsphere;
(3) the linker further comprises SMCC and the heterologous peptide consists of the amino acid sequence KCGGGG (SEQ ID NO:4);
(4) the heterologous peptide is attached to the peptide at the N-terminus of the peptide; and
(5) step (b) is performed by flow cytometry.

59. The method of claim 58, wherein the linker further comprises the heterologous protein BSA, which is directly attached to the carrier, and wherein SMCC is attached (i) to BSA and (ii) via the heterologous peptide to the peptide.

60. The method of claim 51, wherein
(1) the peptide consists of amino acids 9 to 32 of SEQ ID NO:1;
(2) the carrier is a carboxylated microsphere;
(3) the branched amino acid polymer further comprises the short peptide of CK, wherein the short peptide via its C residue is directly attached to the last K residue of the branched amino acid polymer; and
(4) step (b) is performed by flow cytometry.

* * * * *

SEQUENCE LISTING

<160> NUMBER OF SEQ ID NOS: 18

<210> SEQ ID NO 1
<211> LENGTH: 36
<212> TYPE: PRT
<213> ORGANISM: herpes simplex virus 2
<220> FEATURE:
<223> OTHER INFORMATION: herpes simplex virus type 2 (HSV-2)
      glycoprotein G2 (gG-2) amino acids 1-36

<400> SEQUENCE: 1

Pro Gly Ser Pro Ala Pro Pro Pro Glu His Arg Gly Gly Pro Glu
  1               5                  10                  15

Glu Phe Glu Gly Ala Gly Asp Gly Pro Pro Glu Asp Asp Asp Ser
                 20                  25                  30

Ala Thr Gly Leu
         35

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:heterologous
      peptide linker

<400> SEQUENCE: 2

Gly Gly Cys Lys
  1

<210> SEQ ID NO 3
<211> LENGTH: 6
<212> TYPE: PRT
<213> ORGANISM: Artificial Sequence

```
<220> FEATURE:
<223> OTHER INFORMATION: Description of Artificial Sequence:heterologous
      peptide linker

<400> SEQUENCE: 3

Gly Gly Gly Gly Cys Lys
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:heterologous
      peptide linker

<400> SEQUENCE: 4

Lys Cys Gly Gly Gly Gly
 1               5

<210> SEQ ID NO 5
<211> LENGTH: 40
<212> TYPE: PRT
<213> ORGANISM: Artificial Sequence
<220> FEATURE:
<223> OTHER INFORMATION: Description of Artificial Sequence:peptide
      1-SMCC-BSA conjugate
<220> FEATURE:
<221> NAME/KEY: MOD_RES
<222> LOCATION: (40)
<223> OTHER INFORMATION: Xaa = Lys conjugated to
      4-(maleimidomethyl)-1-cyclohexanecarboxylic acid
      (SMCC)-bovine serum albumin (BSA)

<400> SEQUENCE: 5

Pro Gly Ser Pro Ala Pro Pro Pro Pro Glu His Arg Gly Gly Pro Glu
 1               5                  10                  15

Glu Phe Glu Gly Ala Gly Asp Gly Glu Pro Pro Glu Asp Asp Asp Ser
                20                  25                  30

Ala Thr Gly Leu Gly Gly Cys Xaa
            35                  40

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence:peptide
      2-SMCC-BSA conjugate
<220> FEATURE:
<221> NAME/KEY: MOD_RES
<222> LOCATION: (34)
<223> OTHER INFORMATION: Xaa = Lys conjugated to
      4-(maleimidomethyl)-1-cyclohexanecarboxylic acid
      (SMCC)-bovine serum albumin (BSA)

<400> SEQUENCE: 6

Ala Pro Pro Pro Pro Glu His Arg Gly Gly Pro Glu Glu Phe Glu Gly
 1               5                  10                  15

Ala Gly Asp Gly Glu Pro Pro Glu Asp Asp Asp Ser Gly Gly Gly Gly
                20                  25                  30

Cys Xaa

<210> SEQ ID NO 7
<211> LENGTH: 30
<212> TYPE: PRT
<213> ORGANISM: Artificial Sequence
```

```
<220> FEATURE:
<223> OTHER INFORMATION: Description of Artificial
      Sequence:BSA-SMCC-peptide 5  conjugate
<220> FEATURE:
<221> NAME/KEY: MOD_RES
<222> LOCATION: (1)
<223> OTHER INFORMATION: Xaa = Lys conjugated to
      4-(maleimidomethyl)-1-cyclohexanecarboxylic acid
      (SMCC)-bovine serum albumin (BSA)

<400> SEQUENCE: 7

Xaa Cys Gly Gly Gly Gly Pro Glu His Arg Gly Gly Pro Glu Glu Phe
 1               5                  10                  15

Glu Gly Ala Gly Asp Gly Glu Pro Pro Glu Asp Asp Asp Ser
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence:synthetic
      herpes simplex virus type 2 (HSV-2) glycoprotein
      G2 (g

```
<211> LENGTH: 30
<212> TYPE: PRT
<213> ORGANISM: Artificial Sequence
<220> FEATURE:
<223> OTHER IN -continued

```
<400> SEQUENCE: 15

Arg Gly Arg Ala Gly Arg Arg Arg Tyr Ala His Pro Ser Val Arg Tyr
  1               5                  10                  15

Val Cys Leu Pro Pro Glu Arg Asp Gly Gly Gly Gly Cys Lys
             20                  25                  30

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence:synthetic
      herpes simplex virus type 2 (HSV-2) glycoprotein
      G2 (gG-2) peptide 9

<400> SEQUENCE: 16

Arg Arg Arg Tyr Ala His Pro Ser Val Arg Tyr Val Cys Leu Pro Pro
  1               5                  10                  15

Glu Arg Asp Gly Gly Gly Gly Cys Lys
             20                  25

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence:synthetic
      herpes simplex virus type 2 (HSV-2) glycoprotein
      G2 (gG-2) peptide 10

<400> SEQUENCE: 17

Lys Cys Gly Gly Gly Gly Trp Arg Gly Arg Ala Gly Arg Arg Arg Tyr
  1               5                  10                  15

Ala His Pro Ser Val Arg Tyr
             20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence:synthetic
      herpes simplex virus type 2 (HSV-2) glycoprotein
      G2 (gG-2) peptide 11

<400> SEQUENCE: 18

Lys Cys Gly Gly Gly Gly Arg Gly Arg Ala Gly Arg Arg Arg Tyr Ala
  1               5                  10                  15

His Pro Ser Val Arg
             20
```